United States Patent [19]

Ryan et al.

[11] Patent Number: 4,777,260

[45] Date of Patent: Oct. 11, 1988

[54] SYNTHESIS OF NIZATIDINE INTERMEDIATE

[75] Inventors: Charles W. Ryan, Indianapolis; Bruce A. Slomski, Bloomington, both of Ind.

[73] Assignee: Eli Lilly and Company, Indianapolis, Ind.

[21] Appl. No.: 810,456

[22] Filed: Dec. 18, 1985

[51] Int. Cl.$^4$ .......................................... C07D 277/28
[52] U.S. Cl. .................................................... 548/205
[58] Field of Search ........................................ 548/205

[56] References Cited

U.S. PATENT DOCUMENTS

| 4,375,547 | 3/1983 | Pioch | 548/205 |
| 4,382,090 | 5/1983 | Pioch | 548/205 |
| 4,468,399 | 8/1984 | Pioch | 548/205 |

FOREIGN PATENT DOCUMENTS 2111044  6/1983  United Kingdom ............... 548/205

*Primary Examiner*—Robert Gerstl
*Attorney, Agent, or Firm*—Charles W. Ashbrook; Leroy Whitaker

[57] ABSTRACT

The present invention provides a process for preparing a novel intermediate for nizatidine.

1 Claim, No Drawings

SYNTHESIS OF NIZATIDINE INTERMEDIATE

BACKGROUND OF THE INVENTION

Nizatidine is the generic name given to the compound N-[2-[[[2-[(dimethylamino)methyl]-4-thiazolyl]methyl]thio]ethyl]-N'-methyl-2-nitro-1,1-ethenediamine, an anti-ulcer compound taught by Pioch in U.S. Pat. No. 4,375,547. The patent discloses the synthesis of nizatidine by the reaction of 4-[[(2-aminoethyl)thio]-methyl]-N,N-dimethyl-2-thiazolemethanamine with 1,1-dimethylthio-2-nitroethene to provide the corresponding 2-nitro-1-methylthio-1-etheneamine derivative, which is subsequently converted to nizatidine upon reaction with monomethylamine. The process disclosed in the patent produces methanethiol gas as a by-product, which is known to produce an unpleasant odor that requires the use of extra purification equipment to eliminate.

The present invention relates to a process for preparing N-[2-[[[2-[(dimethylamino)methyl]-4-thiazolyl]methyl]thio]ethyl]-2-nitro-1-phenoxy-1-etheneamine comprising reacting 4-[[(2-aminoethyl)thio]methyl]-N,N-dimethyl-2-thiazolemethanamine with 1,1-diphenoxy-2-nitroethene in an aprotic solvent. The present invention also provides the product of the present process as an additional embodiment. The present process does not produce methanethiol gas, and is therefore an especially valuable process for preparing nizatidine on a large scale wherein cost is an important consideration.

SUMMARY OF THE INVENTION

The present invention provides the compound N-[2-[[[2-[(dimethylamino)methyl-]4-thiazolyl]methyl]thio]ethyl]-2-nitro-1-phenoxy-1-etheneamine having the formula

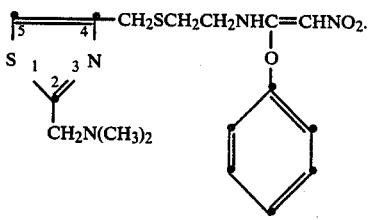

The invention also provides a process for preparing N-[2-[[[2-[(dimethylamino)methyl]-4-thiazolyl]methyl]thio]ethyl]-2-nitro-1-phenoxy-1-etheneamine, having the formula

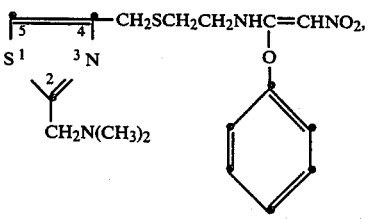

which comprises reacting 4-[[(2-aminoethyl)thio]methyl]-N,N-dimethyl-2-thiazolemethanamine, having the formula

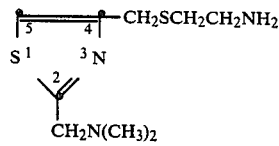

with 1,1-diphenoxy-2-nitroethene in an aprotic solvent.

DETAILED DESCRIPTION OF THE INVENTION

The present process is carried out by combining 1,1-diphenoxy-2-nitroethene with 4-[[(2-aminoethyl)thio]-methyl]-N,N-dimethyl-2-thiazolemethanamine in a suitable reaction vessel. Preferably, a solution of the thiazolemethanamine in isopropyl alcohol is added to a solution of the nitroethene compound dissolved in an aprotic solvent.

Exemplary aprotic solvents include ethers and cyclic ethers such as diethyl ether, 1,2-dimethoxyethane, and tetrahydrofuran, which is preferred; halogenated hydrocarbon solvents such as chloroform and methylene chloride; and related aprotic solvents such as dimethylsulfoxide, N,N-dimethylformamide, sulfolane and acetonitrile. The amount of solvent used in the present process is not critical, but no more than necessary to dissolve the starting thiazolemethanamine and nitroethene product need be used.

The amount of 1,1-diphenoxy-2-nitroethene employed in the present process will be in the range of about one to about two molar equivalents for each molar equivalent of thiazolemethanamine employed. More preferably, the two starting reagents are employed on about an equimolar basis.

The present process is substantially complete after about 10 minutes to about 24 hours when conducted at a temperature in the range of about 0° C. to about 100° C., more preferably after about 30 minutes to about four hours when conducted at a temperature in the range of about 15° C. to about 35° C.

The product of the present process may be isolated by standard procedures, or permitted to undergo additional chemical modification without isolation. If the compound is isolated, the solvent is evaporated, typically under vacuum, and the product purified, if desired, by standard techniques such as crystallization from common solvents or purification over solid supports such as silica gel or alumina.

The process of the present invention has been found to provide the product consistently in high purity so that the compound may be used in the preparation of biologically active compounds without additional expensive purification steps. The present process would have an added advantage in industrial scale synthesis in that it does not produce methanethiol gas as a by-product, a compound which is known to produce an unpleasant odor that requires extra purification equipment to eliminate. The elimination of this stench removes the need for special equipment and handling processes, as well as suitable means of disposal as would otherwise be necessary.

The compound of the present invention is preferably used as an intermediate in the synthesis of nizatidine. Nizatidine may be synthesized from this compound by reaction with monomethylamine, preferably in gaseous form. The reaction is conducted at a temperature in the range of about 20° C. to about 40° C. for a period of about 60 minutes to about 90 minutes. Nizatidine is isolated by evaporating the volatile constituents of the reaction mixture under vacuum and purifying according to standard procedures.

The starting materials employed in the present process are known in the art and readily prepared by prior art processes. The thiazolemethanamine is disclosed in U.S. Pat. No. 4,375,547. The compound 1,1-diphenoxy-2-nitroethene is preferably synthesized by reacting vinylidene chloride with dinitrogen tetroxide and chlorine in a halogenated hydrocarbon solvent at a temperature in the range of about −40° C. to about 0° C. to provide 1,1,1-trichloro-2-nitroethane. See *J. Org. Chem.* 25, 1312 (1960). This compound is dehydrohalogenated with a weak base at ambient temperatures to provide 1,1-dichloro-2-nitroethene, which is finally treated with at least two molar equivalents of sodium phenoxide to provide 1,1-diphenoxy-2-nitroethene. See *Zhurnal Organicheskoi Khimii* 17, 1550 (1981). This compound is typically isolated by standard procedures and recrystallized from isopropyl alcohol.

The following Examples illustrate the synthesis of the compound of the present invention according to the present novel process. The Examples are not intended to be limiting to the scope of the present invention in any respect and should not be so construed.

EXAMPLE 1

Synthesis of Nizatidine

A. N-[2-[[[2-[(Dimethylamino)methyl]-4-thiazolyl]methyl]thio]ethyl]-2-nitro-1-phenoxy-1-etheneamine A solution of 7.07 g (27.5 mmol) of 1,1-diphenoxy-2-nitroethene in 70 ml of tetrahydrofuran was stirred at 25° C. To this solution was added a mixture of 6.83 g (27.5 mmol) of 93% pure 4-[[(2-aminoethyl)thio]methyl]-N,N-dimethyl-2-thiazolemethanamine in 100 ml of isopropyl alcohol. The reaction mixture was stirred for approximately one hour at 25° C. and the progress of the reaction was followed by thin-layer chromatography to provide N-[2-[[[2-[(dimethylamino)methyl]-4-thiazolyl]methyl]thio]ethyl]-2-nitro-1-phenoxy-1-etheneamine. The product was not isolated but rather used directly in the following reaction.

B. Monomethylamine gas was bubbled into the reaction mixture from part A above for twenty minutes during which time the temperature of the mixture rose from about 23° C. to approximately 40° C. Following addition of the gas the reaction mixture was stirred for 30 minutes. The mixture was subsequently concentrated to dryness under reduced pressure. The residual oil was combined with 10 ml of methylene chloride and 80 ml of ethyl acetate to provide a solution upon heating. Seventy milliliters of ethyl acetate were added to the mixture which was slowly cooled to about 25° C. The mixture was heated with a small amount of crystalline product and cooled in an ice bath for approximately 90 minutes. The precipitated solid was collected by vacuum filtration and washed with 70 ml of ethyl acetate. The resulting solid was vacuum dried at 40° C. to provide 6.58 g of nizatidine, N-[2-[[[2-[(dimethylamino)methyl]-4-thiazole]methyl]thio]ethyl]-N'-methyl-2-nitro-1,1-ethenediamine. An assay of the collected material indicated 90.6% pure product to provide a corrected yield of 65.5%. mp=118°–125° C.

EXAMPLE 2

Synthesis of Nizatidine

A. N-[2-[[[2-[(Dimethylamino)methyl]-4-thiazolyl]methyl]thio]ethyl]-2-nitro-1-phenoxy-1-etheneamine A solution of 0.4 g (1.32 mmol) of 85% pure 1,1-diphenoxy-2-nitroethene, 0.35 g (1.52 mmol) of 4-[[(2-aminoethyl)thio]methyl]-N,N-dimethyl-2-thiazolemethanamine, 5 ml of isopropyl alcohol and 5 ml of methylene chloride ws stirred at room temperature for about two hours to provide N-[2-[[[2-[(dimethylamino)methyl]-4-thiazolyl]methyl]thio]ethyl]-2-nitro-1-phenoxy-1-etheneamine in situ. The product was not isolated but used directly in the reaction described in part B.

B. To the reaction mixture prepared by the procedure described in A was added 1.0 ml of 40% aqueous monomethylamine. The reaction mixture was stirred at room temperature for about two hours and the volatile constituents were evaporated under vacuum. The residue was dissolved in 25 ml of methylene chloride and the resulting solution was extracted twice with two 20 ml portions of 1N hydrochloric acid. The acidic extracts were combined and washed with 20 ml of methylene chloride and 25 ml of diethyl ether. The pH of the acidic phase was raised to about 8 with a saturated sodium bicarbonate solution. The aqueous phase was extracted with 25 ml of methylene chloride followed by 10 ml of methylene chloride. The organic phases were combined, dried over anhydrous magnesium sulfate and evaporated under vacuum. The residue was dissolved in isopropyl alcohol. The resulting solution was cooled to provide 0.07 g of nizatidine following vacuum filtration. Yield 16%. mp=125°–135° C.

EXAMPLE 3

According to the general procedure of Example 2, a solution of 1.65 (6.8 mmol) of 95% pure 4-[[(2-aminoethyl)thio]methyl]-N,N-dimethyl-2-thiazolemethanamine and 1.8 g (7.0 mmol) of 1,1-diphenoxy-2-nitroethene dissolved in 25 ml of methylene chloride was stirred at room temperature for about two hours to provide N-[2-[[[2-[(dimethylamino)methyl]-4-thiazolyl]methyl]thio]ethyl]-2-nitro-1-phenoxy-1-etheneamine in situ. This compound was reacted with gaseous monomethylamine to provide 0.8 g of nizatidine. Yield 35.5%.

We claim:

1. The compound N-[2-[[[2-[(dimethylamino)methyl]-4-thiazolyl]methyl]thio]ethy]-2-nitro-1-phenoxy-1-etheneamine having of the formula

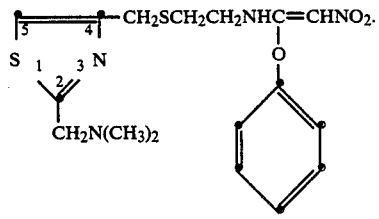

* * * * *

UNITED STATES PATENT AND TRADEMARK OFFICE
CERTIFICATE OF CORRECTION

PATENT NO. : 4,777,260

DATED : October 11, 1988

INVENTOR(S) : Charles W. Ryan and Bruce A. Slomski

It is certified that error appears in the above-identified patent and that said Letters Patent is hereby corrected as shown below:

Claim 1, the second line of the claim,
"thyl]-4-thiazolyl]methyl]thio]ethy]-2-nitro-1-phenoxy-",
should read
--thyl]-4-thiazolyl]methyl]thio]ethyl]-2-nitro-1-phenoxy- --.

Signed and Sealed this

Twenty-first Day of November, 1989

Attest:

JEFFREY M. SAMUELS

Attesting Officer     Acting Commissioner of Patents and Trademarks